US00PP20941P2

(12) United States Plant Patent
Austin

(10) Patent No.: US PP20,941 P2
(45) Date of Patent: Apr. 20, 2010

(54) ***ROSA HYBRIDA* SHRUB NAMED 'AUSVIVID'**

(50) Latin Name: *Rosa hybrida*
Varietal Denomination: AUSvivid

(75) Inventor: David C. H. Austin, Wolverhampton (GB)

(73) Assignee: David Austin Roses Ltd, Albrighton, Wolverhampton (GB)

( * ) Notice: Subject to any disclaimer, the term of this patent is extended or adjusted under 35 U.S.C. 154(b) by 0 days.

(21) Appl. No.: 12/381,394

(22) Filed: Mar. 11, 2009

(30) Foreign Application Priority Data

Nov. 18, 2008 (GB) ..... AFP 5/2107

(51) Int. Cl.
*A01H 5/00* (2006.01)

(52) U.S. Cl. ..... Plt./107

(58) Field of Classification Search ..... Plt./107
See application file for complete search history.

*Primary Examiner*—Annette H Para
(74) *Attorney, Agent, or Firm*—Kauth, Pomeroy, Peck & Bailey LLP

(57) ABSTRACT

A variety of rose plant of the shrub class, named 'AUSvivid' is disclosed. The 'AUSvivid' rose is a plant suitable for repeat flowering having blooms that start as small buds and develop into dome-shape, full-petalled wide open rosettes having a color that is bright and deep pink.

1 Drawing Sheet

CROSS-REFERENCE TO RELATED APPLICATIONS

The current application claims priority to a United Kingdom Breeder's Right Certificate Application No. AFP 5/2107 filed Nov. 18, 2008, the disclosure of which is incorporated herein by reference.

Classification: The present invention relates to a new *Rosa hybrida* shrub.

Variety denomination: The new plant has the varietal denomination 'AUSvivid'.

ORIGIN OF INVENTION

This invention relates to a new and distinct variety of shrub rose plant named 'AUSvivid', which was originated by crossing two unnamed, unpatented varieties of *Rosa hybrida*.

BACKGROUND OF THE INVENTION

The primary objective of this breeding was to produce a flowering variety having small buds that open to full-petalled wipe open rosettes of a bright deep pink. It was also an objective to obtain a bloom with a very light fragrance.

SUMMARY OF THE INVENTION

Among the features which distinguish the new variety from other presently available and commercial rose cultivars known to the inventor is the following combination of characteristics: blooms that start as small buds and develop into dome-shape, full-petalled wide open rosettes having a color that is bright and deep pink.

Asexual reproduction of the new variety by budding as performed in greenhouses at Bowling Green Lane in Albrighton, Britain shows that the foregoing and other distinguishing characteristics come true to form and are established and transmitted through succeeding asexual propagations. 'AUSvivid' may be asexually propagated by budding and grafting. The budding and grafting successfully occurred on the plant/rootstock *Rosa* cv. 'Dr. Huey' in the United States and on the plant/rootstock *Rosa dumetorum* cv. 'Laxa' in the United Kingdom.

COMPARISON WITH PARENTS

The new rose may be distinguished from its seed parent, by the following combination of characteristics: whereas the seed parent has medium-sized pink blooms and upright short growth, 'AUSvivid' produces a small bud that develops into a wide-open full-petalled rosette having a bright, deep pink color. The new variety is classified as a hybrida rose and has a medium-sized bushy shrub with slightly arching habit.

The new variety may be distinguished from its pollen parent, by the following combination of characteristics: whereas the pollen parent bears smaller crimson blooms with few petals, 'AUSvivid' bears flowers having deep, pink blooms that are full-petalled.

COMPARISON WITH THE CLOSEST COMMERCIALLY AVAILABLE CULTIVAR

The closest commercially available cultivar to the new variety is the 'AUSvolume' (U.S. Pat. No. 18,710). The new rose may be distinguished from the 'AUSvolume' variety by the following combination of characteristics: the 'AUSvolume' rose has a larger bloom compared to 'AUSvivid', which has smaller full-petalled bloom. In addition, the 'AUSvolume' variety has a strong Old Rose fragrance, while the 'AUSvivid' has a very light fragrance. Finally, 'AUSvivid' has a much redder new wood color when compared to the wood of the 'AUSvolume' cultivar.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

The following description is of 2 year-old rose plants of the new variety grown outdoors in Albrighton, Britain. Phenotypic expression may vary with environmental, cultural and climatic conditions, as well as differences in conditions of light and soil.

Flower characteristics:

*Blooming habit.*—Recurrent. The number of blooms per plant during the growing season is profuse, but there are too many to count.

*Bud.*—Size: About 2 cm long and 1.7 cm in diameter when the petals start to unfurl. Form: The bud form is pointed ovoid. Color: When sepals first divide, the bud color is Pink Group N66A. When half blown, the upper sides of the petals are Pink Group 66B, and the lower sides of the petals are green-White Group 157A. Calyx: Shape: Flat. Length: 1.2 cm. Diameter: 4.5 cm. Sepals: Arrangement: Regular. Color: Upper Surface: Green Group 143C with Pink Group 67A. Lower Surface: Greyed-Green Group 193A. Length: 1.6 mm. Width: 1 cm. Shape: Broad. Surface texture: Upper Surface: Rough. Lower Surface: Hoary. Number: There are three normally appendaged sepals. There are 2 unappendaged sepals with hairy edges. Receptacles: Color: Green Group 143C. Shape: Funnel. Size: Small, about 0.8 cm tall×1.3 cm wide. Surface: Slightly glandular. Peduncle: Length: Medium, averaging about 5.5 cm. Surface: Glandular. Color: Green Group 143C. Strength: Strong.

*Blooms.*—Size: Medium, average open diameter is about 8 cm. Borne: In clusters of 2–5 blooms having a round shape. Stems: Strength: Normal, average length is about 30 cm. Diameter: 3 mm. Form: When first open, bloom is cupped. Permanence of bloom: becomes more dome-shaped.

*Petalage.*—Number of petals under normal conditions: about 130. Color: The upper sides of the petals are Pink Group N66B. The reverse sides of the petals are Pink Group N66B. The base of the petals has a spot of Yellow Group 1D on both sides. Discoloration: The general tonality at the end of the first day is Pink. Group N66B, the tonality at the end of the third day is Pink Group N66A. With further aging the color changes to: Red-Purple Group 72C. Fragrance: Slight. Character of fragrance: Green.

*Petals.*—Texture: Thin. Size: Width: 3 cm. Length: 3.5 cm. Surface: Smooth. Shape: Oval. Margin: Medium reflexing, weak undulation. Apex Shape: Mid to centre petals: Entire. Outer petals: Notched. Base Shape: Broad. Form: Incurved. Arrangement: Imbricated. Petaloids: Number: 12. Color: Pink Group N66B. Length: 5–12 mm. Width: 8–11 mm. Shape: Irregular. Margin: Irregular. Persistence: Petals drop off cleanly before drying. Lastingness: On the plant: long, about 8 days. As a cut flower: not tested.

*Reproductive parts.*—Stamens: Number: 26 Length: 4 mm. Anthers: Length: 1 mm. Color: Yellow-Orange Group 16A. Arrangement: Regular around styles. Filaments: Color: Yellow-Orange Group 16A. Length: 3 mm. Pollen: Color: Yellow-Orange Group 16A. Pistils: Number: 30. Length: 5 mm. Styles: Color: Green-White Group 155C. Length: 4 mm. Stigmas: Color: Yellow-Orange Group 22A. Length: 1 mm. Hips: None Observed.

Plant characteristics:

*Plant form.*—Shrub.

*Plant growth.*—Medium.

*Age to maturity.*—Two years.

*Mature plant.*—Height: 1 m. Width: 75 cm.

*Rootstock.*—*Rosa* Dr. Huey' for U.S. and *Rosa dumetorum* cv. 'Laxa' for observed plants in the U.K.

*Foliage.*—Number: Leaflets on normal mid-stem leaves: 5 (including terminal leaflet). Size: Medium, about 13 cm long×10 cm wide. Quantity: Normal. Number of leaves per flowering stem: 10. Color: New foliage: Upper side: Green Group 144B, overlaid with Greyed-Red Group 184A. Lower side: Greyed-Red 178B. Old foliage: Upper side: Green Group 137A. Lower side: Green Group 137C.

*Leaflets.*—Size: About 5 cm long×3.8 cm wide. Shape: Broadly oval. Base Shape: Rounded. Apex Shape: Acuminate. Texture: Leathery. Edge: Serrated. Serrations: Single. Petiole: Color: Green Group 137B. Length: 4 cm. Width: 2 mm. Surface Texture: Smooth with prickles. Petiole Rachis: Color: Green Group 137B. Underside: Smooth with prickles. Stipules: Length: 2 cm, hairy. Color: Green Group 137B. Auricle: Shape: Pointed. Length: 5 mm. Width: 2 mm. Color: Green Group 137B. Vein Color: As leaf color Green Group 137B. Venation Pattern: Net-veined.

*Wood.*—New Wood: Color: Greyed-Red Group 178B. Bark: Smooth. Old Wood: Color: Green Group 138A. Bark: smooth.

*Branching habit.*—Number: 10 per main stem. Lateral Branch Dimensions: Length: 30 cm. Diameter: 4 mm.

*Stems.*—Mature Stem: Length: 70 cm. Diameter: 5 mm. Internode Distance: 6 cm. The above measurements are all variable, depending on growing conditions in a season. Stem Pubescence Present: No.

*Prickles.*—Quantity: On main canes from base: Ordinary. Number per stem length: 6 per 10 cm. On laterals from main canes: Ordinary. Number per stem length: 4 per 10 cm. Form: Hooked Downward. Length: 5 mm. Color when young: Red Group 180A. Color when mature: Greyed-Red Group 174A.

*Small prickles.*—Quantity: Main stalk: None. Laterals: None.

*Disease resistance.*—Mildew: Resistant. Blackspot: Resistant. Rust: Resistant.

*Pest resistance.*—Not tested.

*Winter hardiness.*—Not tested.

*Growing conditions.*—Normal.

What is claimed is:

1. A new and distinct variety of rose plant of the shrub class suitable for repeat flower production, substantially as herein shown and described.

* * * * *

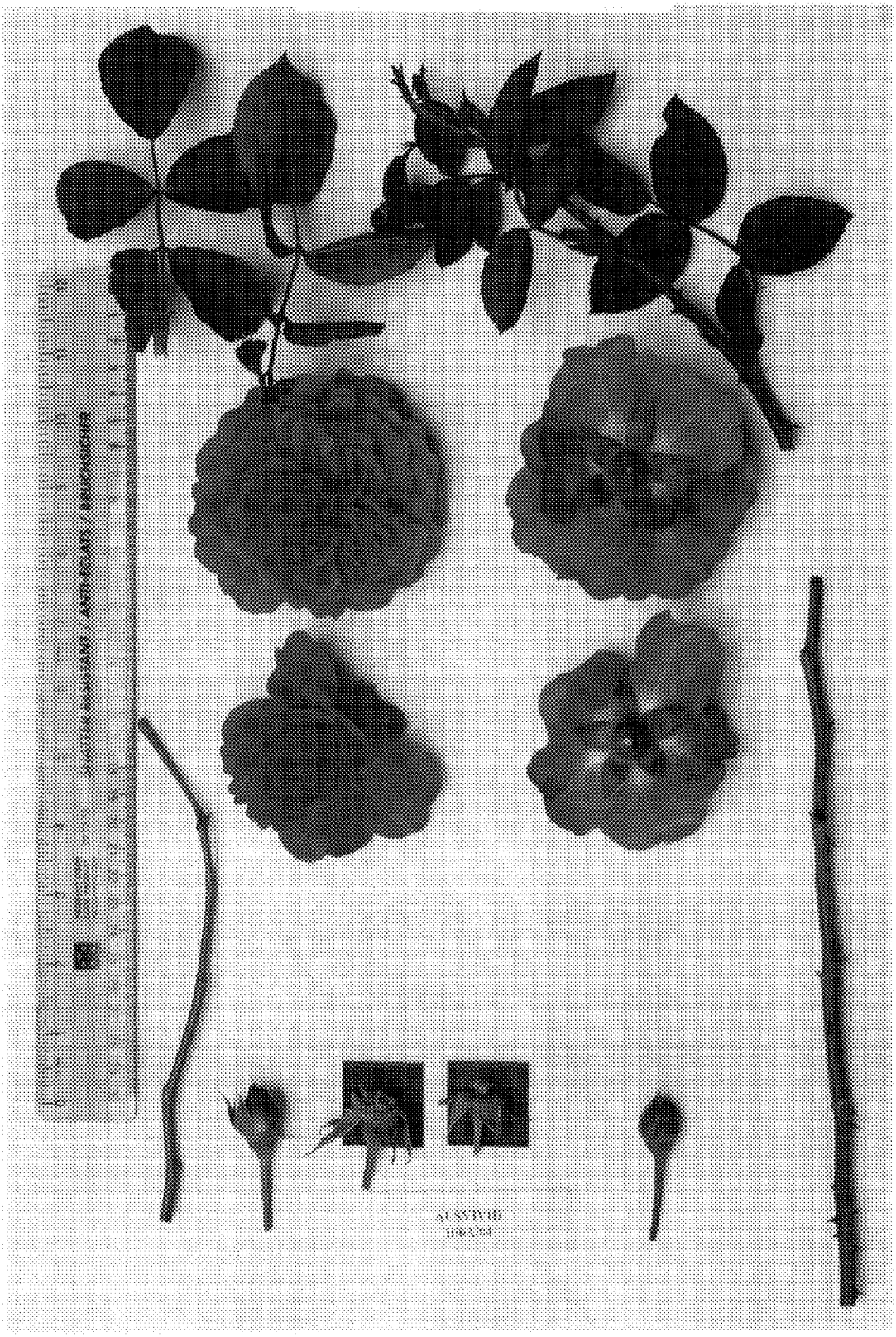

UNITED STATES PATENT AND TRADEMARK OFFICE

CERTIFICATE OF CORRECTION

PATENT NO. : PP 20,941 P2
APPLICATION NO. : 12/381394
DATED : April 20, 2010
INVENTOR(S) : David C. H. Austin It is certified that error appears in the above-identified patent and that said Letters Patent is hereby corrected as shown below:

In column 1, line 22, at the beginning of the line, delete the word "wipe" and insert --wide--

Signed and Sealed this

Fifteenth Day of June, 2010

David J. Kappos

David J. Kappos
*Director of the United States Patent and Trademark Office*